US012751750B2

(12) United States Patent
Sommers et al.

(10) Patent No.: US 12,751,750 B2
(45) **Date of Patent: *Oct. 6, 2026**

(54) BONE SCREW WITH REDUCED FLANK PORTION

(71) Applicant: Acumed LLC, Hillsboro, OR (US)

(72) Inventors: Mark B. Sommers, Beaverton, OR (US); Andrew W. Seykora, Portland, OR (US); Brian R. Conley, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 78 days.

This patent is subject to a terminal disclaimer.

(21) Appl. No.: 18/795,830

(22) Filed: Aug. 6, 2024

(65) Prior Publication Data

US 2024/0390047 A1 Nov. 28, 2024

Related U.S. Application Data

(63) Continuation of application No. 17/592,827, filed on Feb. 4, 2022, now Pat. No. 12,076,065.

(Continued)

(51) Int. Cl.
*A61B 17/86* (2006.01)

(52) U.S. Cl.
CPC ........ *A61B 17/863* (2013.01); *A61B 17/8625* (2013.01); *A61B 17/8645* (2013.01)

(58) Field of Classification Search
CPC .................................................... A61B 17/863
See application file for complete search history.

(56) References Cited

U.S. PATENT DOCUMENTS 5,643,269 A * 7/1997 Harle ...................... F16B 33/02 606/916
6,030,162 A 2/2000 Huebner (Continued)

FOREIGN PATENT DOCUMENTS

| | | | |
|---|---|---|---|
| JP | 2015-171520 | A | 10/2015 |
| WO | 9840024 | A1 | 9/1998 |
| WO | WO 2022/170053 | A1 | 8/2022 |

OTHER PUBLICATIONS

European Extended Search Report corresponding to related European Patent Application No. 22750439.6 dated Nov. 8, 2024, 8 pages.

(Continued)

*Primary Examiner* — Christian A Sevilla
(74) *Attorney, Agent, or Firm* — Knobbe Martens Olson & Bear LLP

(57) ABSTRACT

A bone screw is provided that reduces insertion torque when driving the screw into bone while maintaining pull-out strength. The provided bone screw includes one or more threads having a portion with a reduced flank profile that helps reduce the amount of torque required to drive the bone screw into bone. The portion with the reduced flank profile has an equal thread depth or height as the portion of the one or more threads with a non-reduced flank profile, thereby helping to maintain pull-out strength. The reduced flank profile portion is away from the bone screw's insertion tip. As such, the bone screw's non-reduced flank profile portion creates internal female threads that have a correspondingly larger flank profile than the screw's reduced flank profile portion, thereby reducing friction between the reduced flank profile portion of the one or more threads and the interior female thread.

18 Claims, 7 Drawing Sheets

Related U.S. Application Data

(60) Provisional application No. 63/146,099, filed on Feb. 5, 2021.

(56) References Cited

U.S. PATENT DOCUMENTS

| | | | | |
|---|---|---|---|---|
| 6,129,730 | A | 10/2000 | Bono et al. | |
| 12,076,065 | B2 | 9/2024 | Sommers et al. | |
| 2004/0146834 | A1 | 7/2004 | Haessler | |
| 2008/0015595 | A1 | 1/2008 | Rendard et al. | |
| 2008/0234760 | A1 | 9/2008 | Matulaniec | |
| 2008/0249579 | A1* | 10/2008 | Taylor | A61B 17/863 606/301 |
| 2009/0018589 | A1 | 1/2009 | Smisson et al. | |
| 2011/0045437 | A1 | 2/2011 | Arni | |
| 2014/0277190 | A1 | 9/2014 | Splieth et al. | |
| 2017/0095279 | A1 | 4/2017 | Bare et al. | |
| 2019/0015143 | A1* | 1/2019 | Moreau | A61B 17/864 |
| 2019/0083232 | A1* | 3/2019 | Dacosta | A61B 17/92 |
| 2019/0262047 | A1* | 8/2019 | Sommers | A61B 17/8875 |
| 2020/0093525 | A1* | 3/2020 | Zastrozna | A61B 17/863 |
| 2020/0367951 | A1* | 11/2020 | Rocci | A61B 17/8014 |

OTHER PUBLICATIONS

International Search Report corresponding to related International Patent Application No. PCT/US2022/015250 mailed May 6, 2022, 4 pages.

International Written Opinion corresponding to related International Patent Application No. PCT/US2022/015250 mailed May 6, 2022, 5 pages.

International Preliminary Report corresponding to related International Patent Application No. PCT/US2022/015250 mailed Aug. 17, 2023, 7 pages.

* cited by examiner

BONE SCREW WITH REDUCED FLANK PORTION

PRIORITY CLAIM

The present application is a continuation of U.S. patent application Ser. No. 17/592,827, filed on Feb. 4, 2022, which claims priority to and the benefit of U.S. Provisional Application 63/146,099, filed Feb. 5, 2021, the entireties of each of which are herein incorporated by reference.

BACKGROUND

Certain medical procedures require inserting a screw within a bone. For example, one method of treating a bone fracture is to insert a screw into a bone across the bone fracture, with or without a plate, to hold the bone fragments together as the bone heals. When a surgeon inserts a screw through a bone, frictional forces between the screw's threads and the bone contribute to determining the amount of torque needed to drive the screw into the bone.

Typical bone screws may include a cutting feature at the bone screw's tip portion to cut the thread form of the screw into a bone. Bone screws also typically include threads with a constant outer diameter and uniform threads along the length of the screw. Because of this, once the thread form is created in the bone, the bone screw's remaining threads each interface with the cut region along the bone-screw interface as the bone screw is driven into the bone, thereby generating friction between each of the screw's threads and the bone. As a surgeon drives such typical bone screws into bone, the screws therefore create the same amount of friction between the threads and the bone at any point along the screw. The total amount of friction generated between the typical bone screw and the bone therefore increases with the length of the bone screw because the more threads that contact bone, the higher the cumulative frictional force.

In some instances, such as for long screws that must be driven through a long stretch of bone, the amount of friction generated between the typical screw and the bone, and thus the torque required to drive the typical screw into the bone, may be substantial. The substantial amount of torque required to drive the typical screw into bone may make the procedure more difficult. In some cases, the required torque to drive a typical bone screw, due to the friction it generates, may cause a driving tool to strip the interface between the screw and the driving tool, or to shear off the screw's head. Such damage to the screw may require the screw to be removed and replaced with a new screw, which in some cases can be difficult, and otherwise complicates the procedure. Or, in some cases, the damaged screw cannot be removed and must be left in the bone, which is not desired.

One way to reduce frictional force between a screw and bone, and thus the required insertion torque, is to form a screw with a reduced major diameter. The screw's threads are smaller and thus contact the bone less, creating less friction. A screw with a reduced major diameter, however, also results in the screw having reduced pull-out strength because the threads do not extend as far into the bone. Screw pull-out strength is a key parameter for screw performance in medical procedures because it is important that the screw remain in place within the bone until a surgeon removes it. Therefore, there exists a need for bone screws with reduced torque insertion requirements that do not compromise pull-out strength.

SUMMARY

The present disclosure provides new and innovative bone screws that have a reduced insertion torque when driving the screw into bone as compared to typical bone screws, while maintaining a pull-out strength of the provided bone screws compared to typical bone screws. A portion of the provided bone screw's one or more threads has a reduced flank profile that contributes to the reduced torque required to insert the provided bone screw.

In light of the technical features set forth herein, and without limitation, in a first aspect of the disclosure in the present application, which may be combined with any other aspect unless specified otherwise, a bone screw having a proximal end opposite a distal end is provided. The bone screw includes a first portion adjacent the distal end, a second portion, and a third portion adjacent the proximal end. One or more threads span at least the first and second portions of the bone screw. The one or more threads in the second portion include a reduced flank profile as compared to the one or more threads in the first portion.

In another example, a method is provided for treating a bone fracture that includes installing a bone screw into a bone hole across the bone fracture. The bone screw has a proximal end opposite a distal end, a first portion adjacent the distal end, a second portion, and a third portion adjacent the proximal end. The bone screw includes one or more threads. The one or more threads in the second portion includes a reduced flank profile as compared to the one or more threads in the first portion.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

The present disclosure relates generally to bone screws, and in particular to bone screws with one or more threads that include a portion with a reduced flank profile. The reduced flank profile portion helps reduce the amount of torque required to drive the screws into bone. The reduced flank profile threads are formed with a smaller flank width than the other threads. The threads with the reduced flank profile are away from the end of the screw (e.g., the screw's tip) that is initially inserted into bone. Stated differently, the provided bone screw includes a portion of threads at its insertion end (e.g., tip) that have a flank profile larger than the rest of the screw's threads (e.g., in the screw's shaft). The bone screw may include cutting flutes in this portion with the larger flank profile threads.

The larger flank profile threads at the insertion end or tip create corresponding female threads internal to the bone (e.g., in the generated bone hole) that have a correspondingly larger flank profile than the reduced flank profile threads in the screw's shaft region. As the provided bone screw is driven into the bone, and the shaft's reduced flank profile threads move through the larger internal female threads, friction between the bone and the reduced flank profile threads is therefore reduced because contact between the reduced flank profile threads and the bone is reduced. A flank profile may be reduced in various manners, as described below, to achieve the reduced bone contact. For example, in some aspects, only the outermost tip (e.g., land) of the reduced flank profile threads contact the larger internal female threads of the bone because of their reduced flanks as compared to typical bone screws in which the entire surface of each thread contacts the internal female threads of the bone. The reduction in friction generated by the provided bone screw accordingly reduces the torque required to drive the provided bone screw into the bone. The reduction in required torque accordingly reduces the likelihood that a surgeon strips the screw's head with a driving tool, or shears the screw's head off.

Additionally, in surgical procedures that include inserting a screw within a bone, such to treat a bone fracture, it is important that the screw remains well secured within the bone to provide adequate fixation for the bone to heal. A bone screw must therefore have a high pull-out strength. The provided bone screw's pull-out strength is not affected by the threads having a reduced flank profile because the screw's major diameter remains unchanged. The presently disclosed bone screw accordingly reduces the torque force required to drive the screw into bone while maintaining pull-out strength as compared to typical bone screws.

Figure 1:
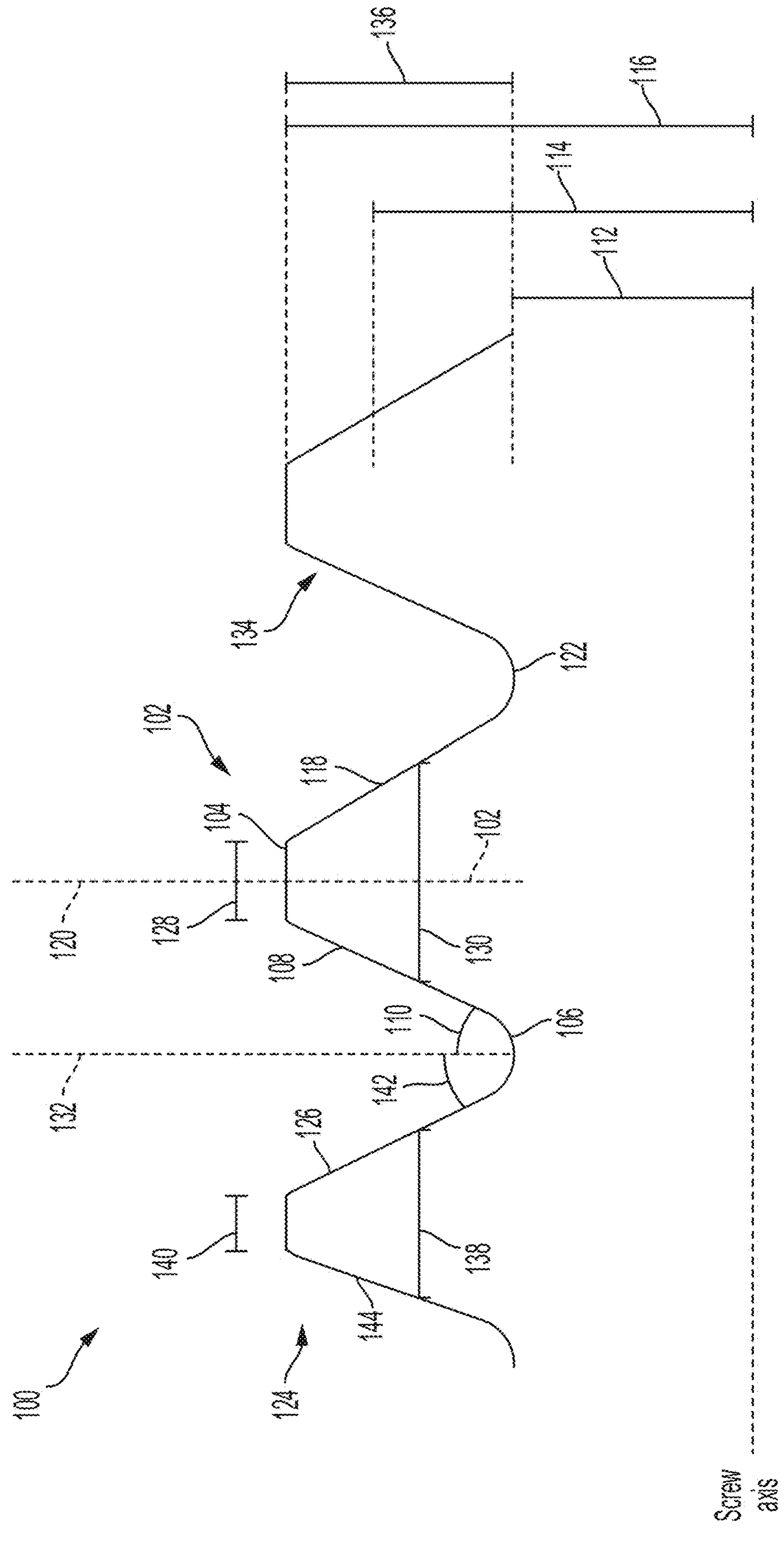
FIG. 1 illustrates a schematic depicting components of a thread form of a screw.
Figure 2:
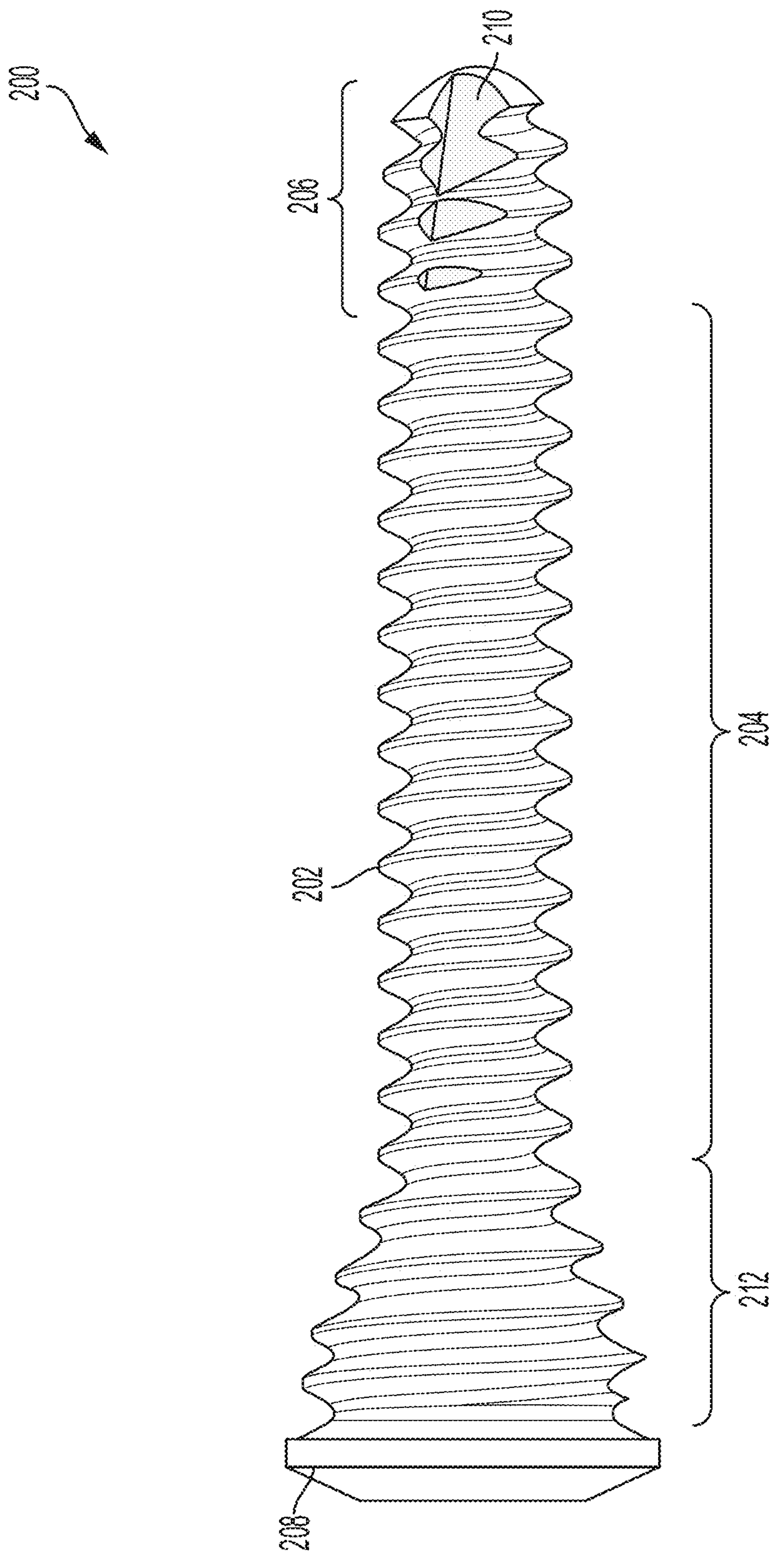
FIG. 2 illustrates an example bone screw with one or more threads having a portion with a reduced flank profile, according to an aspect of the present disclosure.

FIG. 1 illustrates a schematic of an example thread form 100 that depicts various general components of the thread form 100 that are applicable to most or all screws, such as the provided example bone screw 200 (FIG. 2). The thread form 100 includes a thread 102 that includes a land 104, a root 106, and a root 122. The root 106 joins the thread 102 to the next adjacent thread 124. The root 122 joins the thread 102 to the next adjacent thread 134. The land 104 has a land width 128. The thread 102 also includes a flank 108 and a flank 118. The flank 108 is the side of the thread 102 that joins the land 104 and the root 106. The flank 118 is the side of the thread 102 that joins the land 104 and the root 122. The thread 102 can be considered to have a flank angle 110. For example, as illustrated, the flank angle 110 is an angle measured between the flank 108 and a plane 118 perpendicular to the screw's axis.

A flank profile of the thread 102 may be defined by a distance or width 130 between opposing points on the flank 108 and the flank 118 of the thread 102. The distance or width 130 is always perpendicular to the central axis 120 of the thread 102. It will be appreciated that a distance or width 130 will be different among the different opposing points on the flanks 108 and 118 (e.g., measuring a distance or width 130 closer to or farther away from the land 104 along a central axis 120) since the thread 102 is wider near the roots 106 and 122 than the land 104.

Reference is made herein to threads having a smaller or reduced flank profile. As used herein, assuming a distance or width 130 is measured for two different threads at identical positioning along the central axis 120, a thread having a smaller distance or width 130 is considered to have a smaller or reduced flank profile. In at least some instances, a thread having a reduced flank profile has an equal flank angle 110 as the thread having the larger or non-reduced flank profile. In such instances, the land width 128 of the thread having the reduced flank profile is narrower than the land width 128 of the thread having the non-reduced flank profile, to accommodate for the smaller distance or width 130 yet equal flank angle 110. For example, the thread 124 has a smaller or reduced flank profile as compared to the thread 102 and is illustrated having a distance or width 138 measured at identical positioning along the central axis 102 as the distance or width 130 of the thread 102. The distance or width 138 is less than the distance or width 130 due the thread 124 having a land width 140 that is narrower than the land width 128 of the thread 102. Additionally, in this example, the flank angle 142 of the thread 124 is equal to the flank angle 110 of the thread 102.

A screw also includes a minor diameter, which is a measurement that is double a distance 112 between the screw's axis and a root 106. A pitch diameter is a measurement that is double a distance 114 between the screw's axis and a position on a thread 102 where an equal amount of distance exists between the flanks on the solid part of the thread and in the space between the threads. A major diameter is a measurement that is double a distance 116 between the screw's axis and a land 104. Each thread of a screw also includes a thread depth 136 (e.g., thread height).

FIG. 2 illustrates an example bone screw 200 according to an aspect of the present disclosure. In some aspects, the bone screw 200 may be a headless screw. In other aspects, the bone screw 200 includes a screw head 208 at its proximal end. The screw head 108 may take any suitable shape (e.g., flat head, pan head, round head, truss head, oval head, fillister head, bugle head, etc.) and may have any suitable external or internal driver interface (e.g., slotted head, Phillips head, Allen head, square head, security head, hexagon, hexalobe, etc.) to accept a variety of driving tools. The bone screw 200 includes one or more threads 202. The one or more threads 202 can have any suitable configuration (e.g., single lead, dual lead, triple lead, etc.). The example bone screw 200 is illustrated having a single thread 202. In some instances, the one or more threads 202 may cover the entire length of the screw 200 from the screw head 208 to the distal end (e.g., tip) of the screw 200. In other instances, the bone screw 200 may be partially threaded and the one or more threads 202 may cover only a certain distance from the distal end to a position on the screw 200 prior to the screw head 208. The one or more threads 202 can have any suitable thread form (e.g., trapezoidal, standard V, acme, ball, buttress, reverse buttress, worm, etc.). FIG. 2, for example, illustrates the one or more threads 202 having a trapezoidal thread form.

The example bone screw 200 may be constructed of any suitable medical grade material for a surgical screw. For example, the bone screw 200 may be constructed from titanium, stainless steel, cobalt chrome, carbon fiber reinforced plastics, glass fiber reinforced plastics, and other suitable plastics and metals.

In at least some aspects, the one or more threads 202 of the bone screw 200 include a first portion 206, a second portion 204, and a third portion 212. The first portion 206 of the one or more threads 202 is a leading tip region of the bone screw 200 adjacent the distal end of the bone screw 200. The second portion 204 of the one or more threads 202 includes a middle region of the bone screw 200. The third portion 212 of the one or more threads 202 includes a region adjacent the proximal end (e.g., the head 208) of the screw 208. In some aspects, the one or more threads 202 do not include a third portion 212, with that portion of the bone screw 200 instead being unthreaded. Stated differently, in such aspects, the third portion 212 is unthreaded such as with, for example, a non-locking screw. FIG. 2 illustrates one example delineation of the first portion 206, the second portion 204, and the third portion 212 (threaded in this example) of the bone screw 200, though in other examples the bone screw 200 may have other suitable delineations of the first portion 206, the second portion 204, and the third portion 212. For example, the first portion 206 is illustrated including four revolutions of the one or more threads 202. In other examples, the first portion 206 may include more or less than four revolutions of the one or more threads 202, though in any example the first portion 206 is the leading tip region of the bone screw 200. For example, the first portion 206 may include one, two, three, four, five, or six revolutions, or a portion thereof, of the one or more threads 202.

The threads in the second portion 204 of the one or more threads 202 have a reduced flank profile as compared to the threads in the first portion 206 of the one or more threads 202. The reduced flank profile of the second portion 204 of the one or more threads 202 is formed such that the second portion 204 of the one or more threads 202 has a smaller distance or width (e.g., the width 130 of the thread 102) between opposing points on its flanks (e.g., the flanks 108 and 118 of the typical thread 102) as compared to an identical position on the flanks of the first portion 206 of the one or more threads 202. For example, the second portion 204 of the one or more threads 202 may have a narrower land width as compared to the first portion 206 of the one or more threads 202 (e.g., the land width 140 of the thread 124 compared to the land width 128 of the thread 102). The first portion 206 is adjacent the distal end (e.g., leading tip) of the bone screw 200 so that the first portion 206 of the one or more threads 202 having the larger, or non-reduced, flank profile create female threads internal to the bone (e.g., in a bone hole) that have a correspondingly larger flank profile than the second portion 204 of the one or more threads 202 having the reduced flank profile. Friction is therefore reduced between the created internal female threads and the one or more threads 202 having the reduced flank profile as the bone screw 200 is driven into the bone. Friction is reduced because the one or more threads 202 having the reduced flank profile contact the bone less since the internal female threads have a correspondingly larger flank profile than the one or more threads 202 having the reduced flank profile.

In some aspects, the second portion 204 of the one or more threads 202 has an equally reduced flank profile along an entire length of the second portion 204 of the bone screw 200. Stated differently, each revolution of the one or more threads 202 in the second portion 204 has the same flank profile in such aspects-a reduced flank profile. In other aspects, the flank profile of the second portion 204 of the one or more threads 202 may decrease or reduce (e.g., gradually) along at least a segment of the length of the second portion 204. For example, in such other aspects, revolutions of the one or more threads 202 in the second portion 204 may have a larger flank profile closer to the first portion 206 than to the third portion 212.

In at least some aspects, while the second portion 204 of the one or more threads 202 has a reduced flank profile, the second portion 204 of the one or more threads 202 has an equal thread depth (e.g., height) as compared to the first portion 206 of the one or more threads 202. The equal thread depth between the first portion 206 and second portion 204 of the one or more threads 202 enables the land of the one or more threads 202 to contact the interior female thread of a bone hole throughout the first portion 206 and the second portion 204 of the one or more threads 202. Maintaining contact of the land of the one or more threads 202 with the interior female thread in this way helps to maintain pull-out strength of the bone screw 200.

In various instances, the bone screw 200 may include one or more cutting flutes 210. One having skill in the art will appreciate that the one or more cutting flutes 210 are configured to cut a path into bone so that the bone screw 200 may be driven into the bone. As such, the one or more cutting flutes 210 may have other suitable configurations than that illustrated. In some aspects, the first portion 206 of the bone screw 200 corresponds to the one or more cutting flutes 210 such that the first portion 206 terminates at a terminating point of the one or more cutting flutes 210. Stated differently, in such aspects, the second portion 204 of the bone screw 200 begins after the one or more cutting flutes 210 terminate. In other aspects, the second portion 204 of the bone screw 200 may overlap with the one or more cutting flutes 210. In other aspects still, the first portion 206 may extend beyond the termination of the one or more cutting flutes 210.

The third portion 212 of the example bone screw 200, in various aspects, includes a larger major diameter and/or minor diameter than the first portion 206 and the second portion 204 of the bone screw 200. For example, FIG. 2 illustrates one such aspect in which the major and minor diameters of the bone screw 200 gradually increase in the third portion 212 from the interface with the second portion 204 to the head 208. In other aspects, the third portion 212 may include a major or minor diameter equal to that of the second portion 204. In at least some aspects, the one or more threads 202 of the third portion 212 have an equal thread depth (e.g., the thread depth 134 of the thread 102) as the one or more threads 202 in the first portion 206 and the second portion 204. In at least some aspects, the third portion 212 of the example bone screw 200 does not enter the bone when the bone screw 200 is installed. For example, the third portion 212 may instead interface with a plate that is also installed with the bone screw 200. In such aspects, the third portion 212 of the one or more threads 202 may or may not have a reduced flank as compared to the first portion 206 of the one or more threads 202. In some examples, the third portion 212 may be unthreaded as described above.

Figure 3:
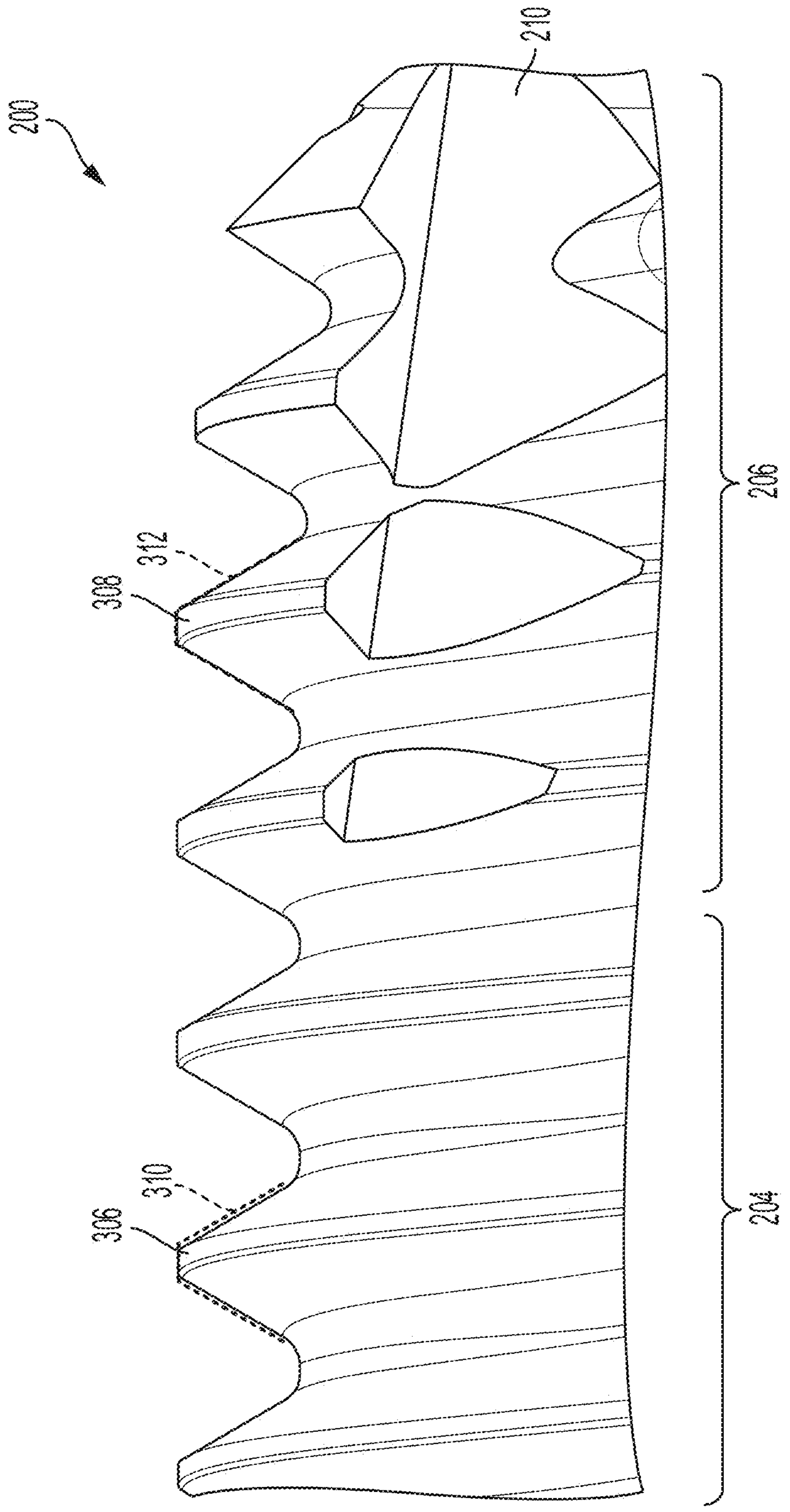
FIG. 3 illustrates a magnified view of a section of the example bone screw of FIG. 2 depicting a thread having a reduced flank profile compared to a thread that does not have a reduced flank profile, according to an aspect of the present disclosure.

FIG. 3 illustrates a magnified view of a section of the example bone screw 200 including the first portion 206 and a segment of the second portion 204. The first portion 206 of the bone screw 200 includes a revolution 308 of the one or more threads 202 and the second portion 204 of the bone screw 200 includes a revolution 306 of the one or more threads 202. The revolution 308, in some instances, may be representative of each revolution of the one or more threads 202 in the first portion 206. The revolution 306, in some instances, may be representative of each revolution of the one or more threads 202 in the second portion 204.

To demonstrate the reduced flank profile of the revolution 306 of the one or more threads 202 in the second portion 204, a flank profile 312 is illustrated outlining the revolution 308 of the one or more threads 202 in the first portion 206, and a flank profile 310 identical to the flank profile 312 is projected over the revolution 306 of the one or more threads 202. As illustrated, there is a gap between the flanks of the revolution 306 of the one or more threads 202 and the flank profile 310 because the revolution 306 of the one or more threads 202 has a reduced flank profile as compared to the revolution 308 of the one or more threads 202. Also illustrated is that the flanks of the revolution 306 are parallel to the flank portions of the flank profile 310 (e.g., the gap is consistent) since, in this example, the revolutions 306 and 308 of the one or more threads 202 have equal flank angles. In this example, the revolution 306 of the one or more threads 202 has a reduced, or shorter/narrower, land width (e.g., the land width 140 of the thread 124 compared to the land width 128 of the thread 102 described above) as compared to the land width of the revolution 308 of the one or more threads 202, which leads to the reduced flank profile of the revolution 306.

In at least some aspects, the flank profile of the revolution 306 of the one or more threads 202 in the second portion 204 is reduced fairly minimally as compared to the flank profile of the revolution 308 of the one or more threads 202 in the first portion 206. For instance, excessively reducing the flank profile of the revolution 306 of the one or more threads 202 can detrimentally compromise the strength of the revolution 306, which could undesirably cause the bone screw 200 to prematurely fail. Additionally, a land of the revolution 306 of the one or more threads 202 must be maintained, which limits the amount that the flank profile of the revolution 306 of the one or more threads 202 can be reduced. As such, the flank profile of the revolution 306 of the one or more threads 202 in the second portion 204 is reduced just enough to sufficiently reduce or eliminate contact between the respective flanks of the revolution 306 of the one or more threads 202 and an interior female thread (e.g., in a bone hole) created by the revolution 308 of the one or more threads 202 in the first portion 206. While contact is reduced or eliminated between the flanks of the revolution 306 and the interior female thread, the land of the revolution 306 still contacts the interior female thread during installation of the bone screw 200.

Figure 4:
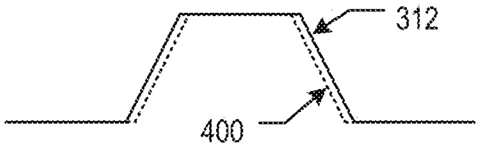
FIG. 4 illustrates the reduced flank profile of FIG. 3 compared to a non-reduced flank profile, according to an aspect of the present disclosure.

As mentioned above, a thread's flank profile may be reduced in various manners. In one aspect, as described above in connection with FIGS. 1 to 3, both of a thread's flanks may be reduced such that neither of the thread's flanks contact an interior female thread formed by the bone screw's leading portion. FIG. 4 further illustrates this aspect by showing a flank profile 400 of the revolution 306 as compared to the flank profile 312 of the revolution 308. As illustrated, the flanks of the flank profile 400 are parallel to their respective flanks of the flank profile 312. In other examples, one of the flanks of the flank profile 400 may be non-parallel to (i.e. have a different flank angle than) its respective flank of the flank profile 312, or both flanks of the flank profile 400 may be non-parallel to (i.e. have a different flank angles than) their respective flanks of the flank profile 312 (see FIG. 7).

Figure 5:
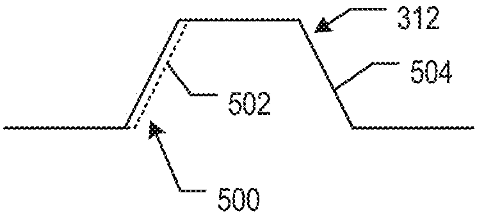
FIG. 5 illustrates a one-sided reduced flank profile compared to a non-reduced flank profile, according to an aspect of the present disclosure.

In another aspect, a thread having a reduced flank profile may have only one flank that is reduced. For example, FIG. 5 illustrates a flank profile 500 of a thread revolution as compared to the flank profile 312 of the revolution 308. As illustrated, while the flank 502 of the flank profile 500 is reduced compared to the flank profile 312, the flank 504 is not reduced and thereby overlaps the flank profile 312. In at least some aspects, the reduced flank 502 is on the leading side of the thread revolution while the non-reduced flank 504 is on the trailing side of the thread revolution. In this way, as a bone screw (e.g., the bone screw 200) is driven into bone, friction is reduced between the thread revolution having the reduced flank profile and the bone because the leading side of the thread revolution, which is pressed into the bone during insertion, does not contact the bone. The trailing side of the thread revolution that still contacts the bone during insertion contributes little to the insertion torque. The torque required to insert the bone screw 200 with a portion of its thread(s) having the flank profile 500 is thereby reduced as compared to typical bone screws. In some examples, each thread revolution in the portion of the thread(s) having a reduced flank profile (e.g., the second portion 204) may have the flank profile 500.

Figure 6:
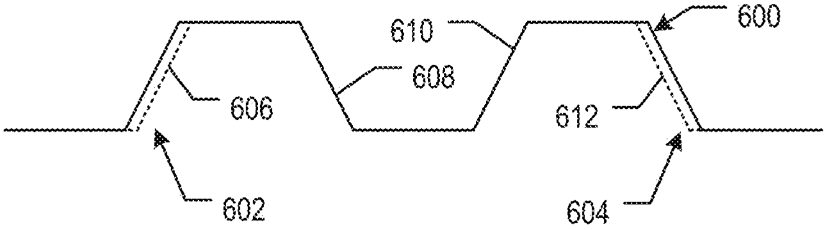
FIG. 6 illustrates a mirrored reduced flank profile compared to a non-reduced flank profile, according to an aspect of the present disclosure.

In another aspect, at least some of the thread revolutions in the reduced flank profile portion (e.g., the second portion 204) of thread(s) of a bone screw (e.g., the bone screw 200) may have mirrored reduced flanks, such as that illustrated by FIG. 6. A flank profile 600 of adjacent non-reduced thread revolutions is illustrated overlapped with reduced flank profiles 602 and 604. As shown, the reduced flank profile 602 includes a reduced flank 606 on a trailing side of the thread revolution and a non-reduced flank 608 on the leading side. Conversely, the reduced flank profile 604 includes a non-reduced flank 610 on the trailing side and a reduced flank 612 on the leading side. The mirrored reduced flanks of the reduced flank profile 602 may be beneficial, for example, if the bone screw 200 is installed across a fracture with the thread revolutions having the reduced flank profiles 602 and 604 on opposite sides of the fracture. In such an example, the thread revolution having the flank profile 602 may push the bone fragment within which it is installed towards the other bone fragment. Likewise, the thread revolution having the flank profile 604 may push the bone fragment within which it is installed towards the other bone fragment (i.e. the opposite direction of the thread revolution having the flank profile 602).

Figure 7A:
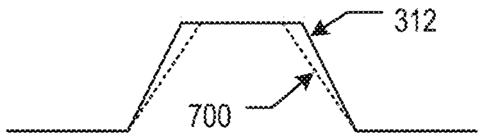
FIGS. 7A and 7B illustrates non-parallel reduced flank profiles compared to a non-reduced flank profile, according to an aspect of the present disclosure.
Figure 7B:
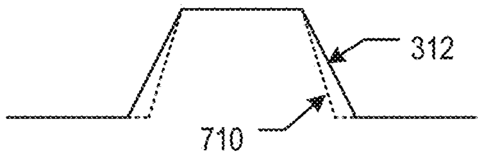

In another aspect, a thread having a reduced flank profile may have reduced flanks with a flank angle that is different from a corresponding non-reduced flank profile. For example, FIG. 7A illustrates a flank profile 700 of a thread revolution as compared to the flank profile 312 of the revolution 308. As shown, the flanks of the flank profile 700 are non-parallel to the flanks of the flank profile 312. This is because the flanks of the flank profile 700 have a different flank angle than the flanks of the flank profile 312. Additionally, the flank profile 700 includes a narrower land than the flank profile 312. In another example, FIG. 7B illustrates a flank profile 710 that includes an equal land width as the flank profile 312 while also having flanks with a different flank angle than the flanks of the flank profile 312. The flank profile 710 includes an equal land width with the flank profile 312. In some aspects, only one flank of the flank profiles 700 and 710 may be reduced (e.g., similar to the flank profile 500).

Figure 8:
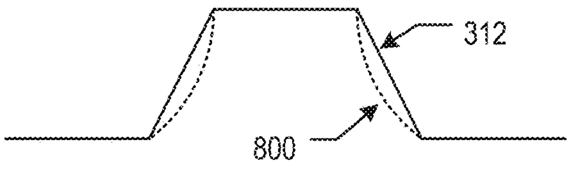
FIG. 8 illustrates a non-linear reduced flank profile compared to a non-reduced flank profile, according to an aspect of the present disclosure.

In another aspect, a thread having a reduced flank profile may have reduced flanks that are nonlinear. For example, FIG. 8 illustrates a flank profile 800 of a thread revolution as compared to the flank profile 312 of the revolution 308. As shown, the flanks of the flank profile 800 are curved. In other examples, one or both flanks of the flank profile 800 may have other suitable, nonlinear shapes. In some aspects, only one flank of the flank profile 800 may be reduced (e.g., similar to the flank profile 500).

In various aspects, each thread revolution of the example bone screw 200 in the portion of the thread(s) having a reduced flank profile (e.g., the second portion 204) may have the same type of reduced flank profile. For example, each thread revolution may have the flank profile 500. In other aspects, the example bone screw 200 may have more than one type of reduced flank profile in its second portion 204. For example, one or more thread revolutions in the second portion 204 may have the flank profile 500 and one or more different thread revolutions in the second portion 204 may have the flank profile 800. In another example, a first thread in the second portion 204 may have the flank profile 700 and a second thread in the second portion 204 may have the flank profile 710.

Figure 9:
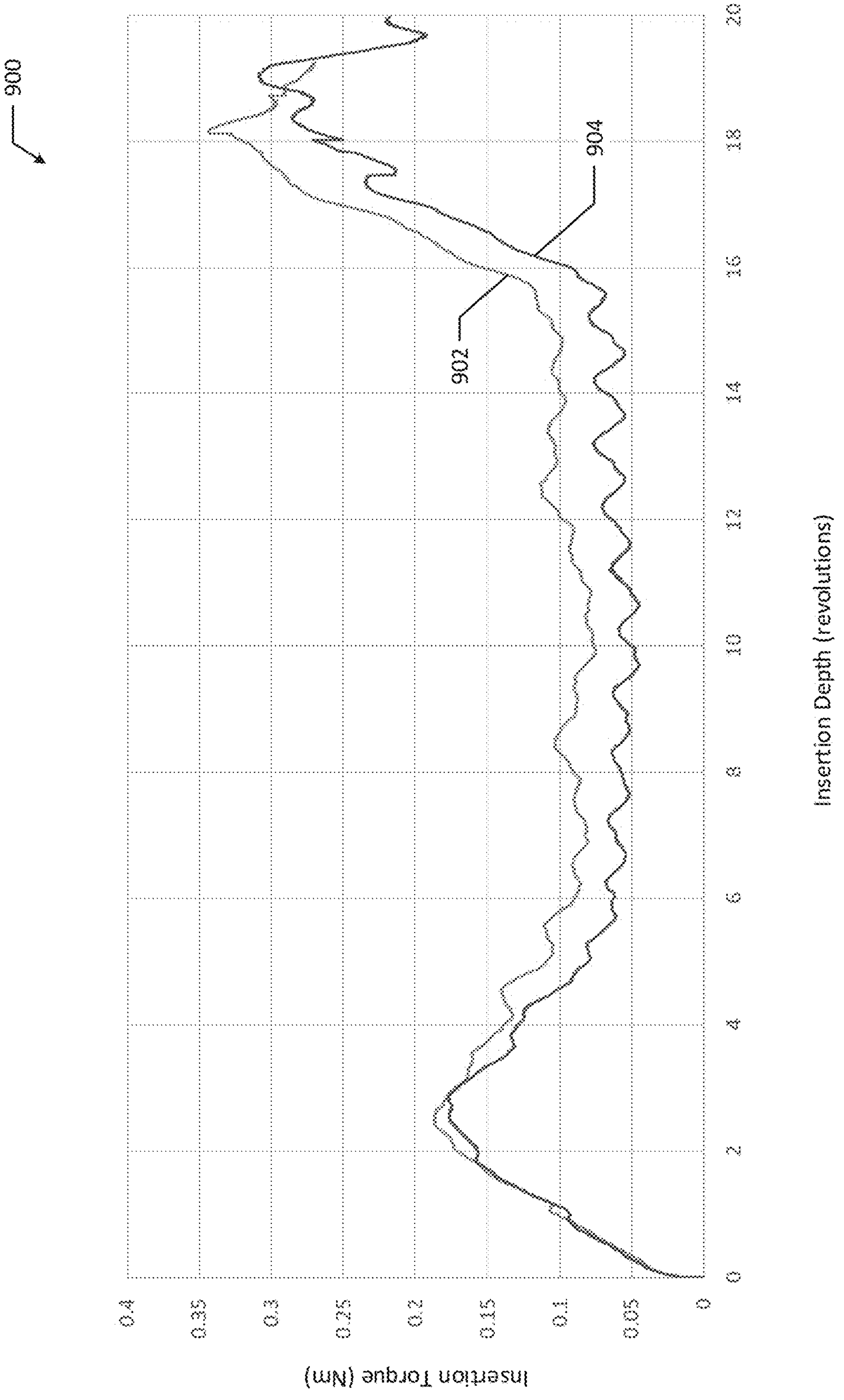
FIG. 9 illustrates a graph showing an expected performance of a typical bone screw compared to an example bone screw with one or more threads having a portion with a reduced flank profile.

FIG. 9 illustrates a graph 900 that shows an expected performance of a typical bone screw by the line 902 in comparison to the expected performance of the provided bone screw (e.g., the bone screw 200) that has a reduced flank portion (e.g., the second portion 204) by the line 904. Initially, when each screw penetrates the first cortex, the torque needed to install each screw can be fairly identical. This is because the first portion 206 of the one or more threads 202 of the example bone screw 200 can be identical to a typical bone screw. Stated differently, the flank profile of the first portion 206 of the one or more threads 202 of the example bone screw 200 is not reduced. Subsequent to this initial insertion, however, when each screw is driven through cancellous bone and penetrates the second cortex, the torque needed to install the provided bone screw 200 is consistently lower than a typical bone screw (i.e. the line 904 is below the line 902). This is because, subsequent to the initial insertion, the second portion 204 of the one or more threads 202 of the example bone screw 200 enters the bone hole. The second portion 204 of the one or more threads 202 has a reduced flank profile, which results in less contact, and therefore less friction, between the second portion 204 of the one or more threads 202 and the bone hole's interior female thread as compared to the typical bone screw's threading.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A bone screw having a proximal end opposite a distal end, the bone screw comprising:

a first portion adjacent the distal end, a second portion, and a third portion adjacent the proximal end; and one or more threads spanning at least the first and second portions of the bone screw, wherein the one or more threads in the second portion include a reduced flank profile as compared to the one or more threads in the first portion;

wherein the one or more threads in the first portion and the one or more threads in the second portion have an equal thread depth;

wherein the one or more threads extend from the proximal end to the distal end.

2. The bone screw of claim 1, wherein each revolution of the one or more threads in the second portion includes an equally reduced flank profile.

3. The bone screw of claim 1, wherein the respective flank profiles of each revolution of the one or more threads in the second portion gradually reduce with respect to one another from an interface of the second portion and the first portion and towards the proximal end.

4. The bone screw of claim 1, wherein the bone screw is a headless bone screw.

5. The bone screw of claim 1, wherein the one or more threads in the second portion including the reduced flank profile have at least one curved flank.

6. The bone screw of claim 1, wherein the one or more threads in the second portion including the reduced flank profile have one reduced flank and one non-reduced flank.

7. The bone screw of claim 1, wherein the first portion of the bone screw includes one or more cutting flutes, and wherein the first portion of the bone screw terminates at a terminating point of the one or more cutting flutes.

8. The bone screw of claim 1, wherein the third portion of the bone screw has a larger major diameter than the second portion of the bone screw.

9. The bone screw of claim 8, wherein the one or more threads span the third portion of the bone screw, and wherein the one or more threads in the third portion have an equal thread depth with the one or more threads in the second portion.

10. The bone screw of claim 1, wherein the one or more threads are configured such that the bone screw is a dual lead or a triple lead screw.

11. The bone screw of claim 1, wherein a thread form of the one or more threads is one selected from the group consisting of trapezoidal, standard V, acme, ball, buttress, reverse buttress, and worm.

12. The bone screw of claim 1, wherein the one or more threads include a land width, and wherein the one or more threads in the second portion including the reduced flank profile have a narrower land width than the one or more threads in the first portion.

13. The bone screw of claim 1, wherein the second portion includes a greater proportion of a length of the bone screw than the first portion.

14. A method for treating a bone fracture comprising:

installing the bone screw of claim 1 into a bone hole across the bone fracture.

15. The method for treating a bone fracture of claim 14, wherein the one or more threads in the second portion generates less friction with the bone hole during installation than the one or more threads in the first portion.

16. The method for treating a bone fracture of claim 14, wherein only a land of the one or more threads in the second portion contacts the bone hole during installation.

17. The method for treating a bone fracture of claim 14, further comprising installing a plate with the bone screw.

18. The method for treating a bone fracture of claim 14, wherein the first and second portions of the bone screw are installed into the bone hole, but the third portion of the bone screw is not installed into the bone hole.

* * * * *